United States Patent
McCarter et al.

(10) Patent No.: US 7,110,920 B2
(45) Date of Patent: Sep. 19, 2006

(54) WATER MONITORING SYSTEMS

(75) Inventors: Steven M. McCarter, York, PA (US); Ronald W. Jenkins, York, PA (US)

(73) Assignee: BAE Systems Land & Armaments L.P., Arlington, VA (US)

( * ) Notice: Subject to any disclaimer, the term of this patent is extended or adjusted under 35 U.S.C. 154(b) by 168 days.

(21) Appl. No.: 10/899,438

(22) Filed: Jul. 26, 2004

(65) Prior Publication Data

US 2005/0065755 A1 Mar. 24, 2005

Related U.S. Application Data

(60) Provisional application No. 60/490,062, filed on Jul. 24, 2003.

(51) Int. Cl.
*G06F 15/00* (2006.01)
(52) U.S. Cl. .................. 702/188; 702/31; 702/189; 422/68.1; 422/58; 422/82.07; 73/152.18; 73/152.29
(58) Field of Classification Search ............ 702/31–32, 702/188–189; 422/68.1, 58, 82.07, 82.08; 73/152.18, 152.29
See application file for complete search history.

(56) References Cited

U.S. PATENT DOCUMENTS

| | | |
|---|---|---|
| 4,626,992 A | 12/1986 | Greaves et al. |
| 5,646,863 A | 7/1997 | Morton |
| 6,058,763 A | 5/2000 | Shedd et al. |
| 6,131,451 A * | 10/2000 | Izbicki et al. ............ 73/152.18 |
| 6,393,899 B1 | 5/2002 | Shedd et al. |
| 6,569,384 B1 * | 5/2003 | Greenbaum et al. ....... 422/68.1 |

OTHER PUBLICATIONS

Bower et al., 'Multi-Computer Acquisition and Processing for Marine Environmental Monitoring', 1986, IEEE Publication, pp. 234-241.*
Sanders et al., 'Stand-Off Tissue-Based Biosensors for the Detection of Chemical Warfare Agents Using Photosynthetic Fluorescence Induction', Jan. 16, 2001, Biosensors & Bioelectronics Publication, pp. 439-446.*
Leather et al., 'Containment Flux Measurements Across Sediment Water Interface in San Diego Bay', 1999, Computer Sciene Corporation, pp. 1700-1713.*

(Continued)

*Primary Examiner*—Marc S. Hoff
*Assistant Examiner*—Elias Desta
(74) *Attorney, Agent, or Firm*—Patterson, Thuente, Skaar & Christensen, P.A.

(57) ABSTRACT

Improved water monitoring systems comprise a test unit having an analytical device and a control system in communication with the test unit such that water supply data generated at the test unit can be communicated to the control system. In some embodiments, the analytical device can be a fluorometer that can monitor the fluorescence induction pattern of algae located in the water, which can indicate, when the induction pattern is compared against known baseline induction patterns, the potential presence of toxic chemicals located in the water supply. In other embodiments, the analytical device can comprise, for example, a pH meter, an infrared spectroscopy (IR) device or the like. In some embodiments, the test unit can provide continuous intake, analysis, and can communicate water supply data to the control system via a wireless communication device, fiber optic cable or the like.

16 Claims, 7 Drawing Sheets

OTHER PUBLICATIONS

Kennedy et al., 'Methods for Collecting High-Frequency Geographically Referenced in situ Water Quality Information', Mar. 1999, Water Quality Note Publication, AM-01, pp. 1-7.*

Postolache et al., 'An Internet and Microcontroller-Based Remote Operation Multi-Sensor System for Water Quality Monitoring', Jan. 2002, IEEE Publication, pp. 1532-1536.*

* cited by examiner

WATER MONITORING SYSTEMS

CROSS-REFERENCE TO RELATED APPLICATIONS

The current application claims the benefit of priority from U.S. Provisional Patent Application filed on Jul. 24, 2003, entitled "Water Supply Monitoring Device and Method" having Ser. No. 60/490,062, which is hereby incorporated by reference herein.

FILED OF THE INVENTION

The present invention relates to devices and methods for monitoring a supply of drinking water, and more particularly, to such devices and methods that can remotely monitor the presence of toxic agents in one or more water supplies.

BACKGROUND OF THE INVENTION

Supplies of drinking water for domestic civilian consumption, as well as those for deployed military forces, are vulnerable to being contaminated with potentially toxic chemicals, such as nerve agents, blood agents, and concentrations of herbicides and/or pesticides. All of these chemicals when present in sufficient amounts can be detrimental to the health of anyone who drinks the contaminated water. In order to reduce the chances that the population, whether civilian or military, will consume contaminated water, it is important to quickly detect toxic chemicals and other dangerous impurities at the primary source of the water, i.e., the reservoir, river or lake, before substantial amounts of the contaminated water can be distributed to the ultimate consumers.

It has been discovered that naturally occurring biosensors such as, for example, algae and cyanobacteria, which are present in all surface water exposed to sufficient sunlight, can be potentially useful biosensors. In general, algae is ubiquitous and can grow year round in most climactic conditions. In addition, algae can survive on low concentrations of nutrients and/or on nutrients that are in forms unsuitable for large multi-cellular organisms. Thus, algae can be an ideal biosensor since it's found in virtually all surface water sources and can survive and reproduce without significant human maintenance.

In general, it is known that there is a correlation between the photosynthetic activity of plants and measurable fluorescence induction spectrums of plants. Additionally, it is also known that a change in the fluorescence induction spectrum or pattern of a plant can represent a change in photosynthetic capability, which can be caused by the presence of toxic chemicals. Furthermore, as described above, all natural sources of water exposed to sufficient sunlight contain algae, which produce characteristic fluorescence induction patterns during normal photosynthetic activity.

Recently, there has been an increased awareness that surface water, such as rivers, lakes and the like, could potentially be the target of terrorist attacks. More specifically, the public accessibility of most surface water sources increases the possibility that a chemical and/or biochemical toxin could be released into the water supply without being immediately detected. Additionally, with the large quantity of pesticides and herbicides employed by modern society, it is possible that an unknown, accidental leak of a toxin could occur that could pose significant health risks. The large number of water sources, along with the relative size of the water sources, also makes continuous human monitoring and testing of surface water sources a cumbersome, expensive and potentially impossible task. The water monitoring industry, as well as the federal government, has searched for a simple biosensor that can be used to detect toxins present in water sources. Thus, it would be desirable to provide a water source monitoring system that could continuously monitor water sources and reduce the need for humans to travel to a particular water source site for testing and analysis of the water.

SUMMARY OF THE INVENTION

In a first aspect, the invention pertains to a water supply monitoring system comprising a test unit having a housing, a plumbing system that can intake water from a water source into the housing, a fluorometer located within the housing connected to the plumbing system, and a control module comprising a first computer processor and a first data link operably connected to the first computer processor. The plumbing system can provide a fluid flow pathway to the fluorometer, and the fluorometer can be operably connected to the first data link such that fluorescence induction data generated by the fluorometer can be communicated to the first data link. In these embodiments, the water supply monitoring system can further comprise a remotely located control system comprising a second data link in communication with the first data link, a second computer processor operably connected to the second data link, and a control and display panel operably connected to the computer processor, wherein the first data link can communicate the fluorescence induction data to the second data link, and wherein the fluorescence induction data can be communicated from the second data link to the second computer processor.

In another aspect, the invention relates to a method of monitoring a water supply comprising communication fluorescence induction data of a water sample generated by a test unit to a remotely located control system. In these embodiments, the control system can comprise a control and display panel, a computer processor and a data link, wherein the computer processor can be operably connected to the data link such that signals received by the data link can be communicated to the computer processor, and wherein the control and display panel is operably connected to the computer processor to receive signals form the computer processor.

DETAILED DESCRIPTION OF THE INVENTION

Improved water monitoring systems comprise a test unit having an analytical device and a control system in communication with the test unit such that water supply data generated at the test unit can be communicated to the control system. In some embodiments, the analytical device can be a fluorometer that can monitor the fluorescence induction pattern of algae located in the water, which can indicate, when the induction pattern is compared against known baseline induction patterns, the potential presence of toxic chemicals located in the water supply. In other embodiments, the analytical device can comprise, for example, a pH meter, an infrared spectroscopy (IR) device or the like. In some embodiments, the test unit can provide continuous intake, analysis, and can communicate water supply data to the control system via a wireless communication device, fiber optical cable or the like. In some embodiments, a plurality of test units can be in communication with a single remotely located control system, which can facilitate monitoring of one or more water sources from a centralized location such as, for example, a water treatment facility or the like. Additionally, the combination of the test unit(s) and the remotely located control system can reduce or eliminate the need for individuals to travel to a particular water supply site in order to monitor water quality and/or purity. In some embodiments, the control system can comprise an alarm system that can provide an audio and/or visual alert if an unusual, or deviant, test pattern is detected.

It is known that a correlation exists between photosynthetic activity of plants and fluorescence induction pattern of plants, so that a chemical and/or biochemical toxin in contact with a plant can alter the fluorescence induction pattern of the plant, which makes plants potentially useful biosensors. Algae is present in all natural water sources that receive sufficient sunlight, and therefore algae can be a useful biosensor for the detection of toxic chemicals and/or biochemicals present in water sources. Different chemical and/or biochemical agents can have different effects (i.e., some chemicals can cause an increase, while others can cause a decrease) upon the fluorescence pattern of a particular algae. As such, the particular deviation from a standard, or baseline, fluorescence pattern can also indicate, when compared against known toxin/water fluorescence patterns, the potential toxin causing the deviation. Detecting the presence of chemicals in water by analyzing the photosynthetic activity of naturally occurring photosynthetic organism, such as, for example, algae, in water is described in U.S. Pat. No. 6,569,384 to Greenbaum et al., entitled "Tissue-Based Water Quality Biosensors For Detecting Chemical Warfare Agents," which is hereby incorporated by reference herein.

In some embodiments, the present disclosure relates to a monitoring system capable of continuously monitoring one or more water supplies such that real time detection of potential chemical and/or biochemical toxins can be monitored from a single location. Generally, the monitoring systems of the present disclosure can comprise one or more test units located at one or more desired water supply sites such that the test units can continuously intake, analyze and expel water located at the desired water site. The test units can further comprise an analytical device such as, for example, a fluorometer connected to the plumbing, or intake, system of each of the test units, which facilitates introducing water into the analytical device for analysis. In some embodiments, the analysis can comprise measuring the fluorescence induction pattern of algae contained within the water sample. Additionally, the measured algae fluorescence pattern of the water sample can be compared to known fluorescence patterns for the particular water supply and/or algae located within the water supply, to determine if a potential toxin is located in the water sample. The water supply monitoring system can further comprise a control system which can be in communication with the test units such that water supply data generated by the test units can be transmitted to the control unit, which can facilitate the real time monitoring of one or more water supply sites from a centralized location. In some embodiments, the control system can be a remotely located control system located at, for example, a water treatment facility, government regulatory agency, local law enforcement agency or the like.

Figure 1:
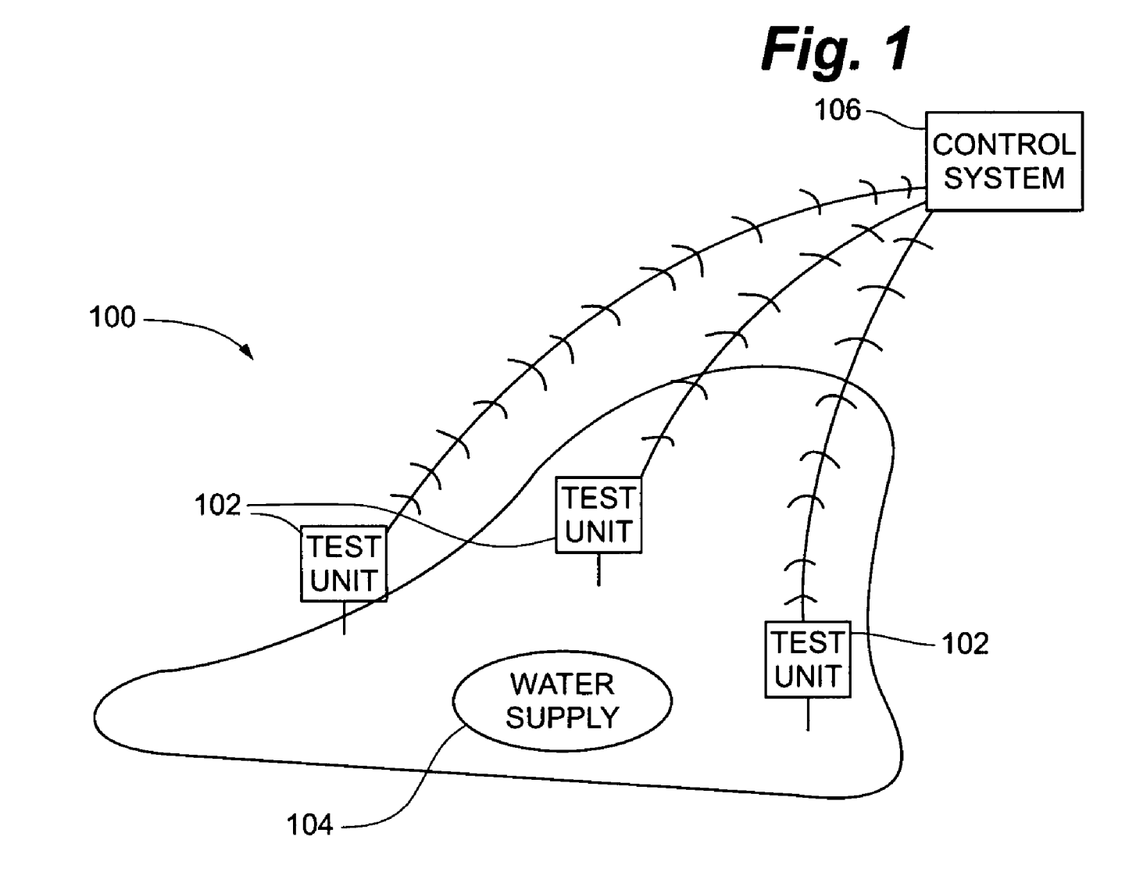
FIG. 1 is a schematic diagram of a water monitoring system comprising a test unit in communication with a remotely located control unit.

Referring to FIG. 1, a water monitoring system 100 is shown comprising one or more test units 102 positioned in communication with water supply 104, which facilitates intake of water from water supply 104 into test units 102. Additionally, the test units 102 of the present disclosure can further comprise communication equipment, such as, for example, wireless communication equipment, to communicate with control system 106. Although FIG. 1 shows an embodiment where three test units 102 are located at water supply site 104, one of ordinary skill in the art will recognize that no particular number of test units are required by the present disclosure. Additionally, the number of test units located at a particular water supply site can be guided by the location and relative size of the particular water supply site. For example, larger water supply sites and/or water supply sites that are easily accessible may have more test units relative to water supply sites that are smaller and/or are located in hard to access areas. Although FIG. 1 shows test units 102 positioned directly over water supply site 104, in other embodiments test units 102 can be located proximate water supply site 104. In other words, it is not necessary for test units 102 to be located in or directly over the water supply site, as long as test units 102 can intake water from the water supply site. For example, the test units can be located on land near a desired water supply site, and a hose, pump or other plumbing system can be employed to facilitate intake of water from the water supply site into the test unit.

Figure 2A:
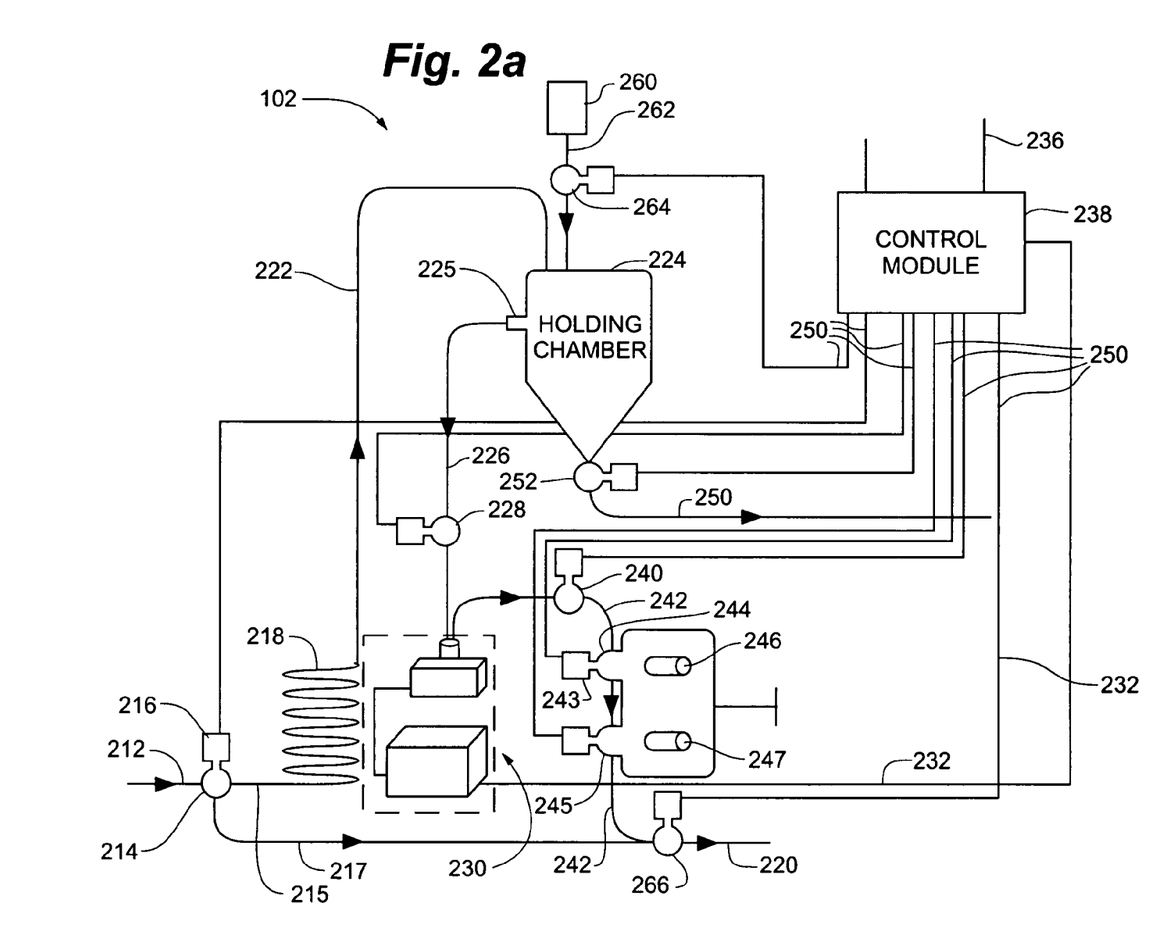
FIG. 2a is a schematic diagram of a test unit that can be employed in the water monitoring systems of the present disclosure.

Referring to FIG. 2a, an embodiment of a test unit 102 suitable for use in the water monitoring systems of the present disclosure is shown comprising a water intake line 212 connected to the output of a conventional pump (not shown). The intake of the conventional pump can be in free communication with, and can draw water from, a desired water supply site. As shown in FIG. 2a, valve 214, and associated solenoid 216, can regulate fluid flow between a first position, in which intake line 212 is connected to tubing coil 218 via line 215, and a second position in which intake line 212 is connected to discharge line 220 via line 217. In some embodiments, tubing coil 218 can be connected by holding chamber input line 222 to holding chamber 224, from which desired quantities of water samples can be directed to fluorometer 230 through holding chamber output line 226, which can be connected to side arm 225. The flow of water from holding chamber 224 to fluorometer 230 can be regulated by input valve 228, which facilitates introducing desired amounts of water into fluorometer 230 at desired time intervals. In general, the fluorometers employed in the water monitoring systems of the present disclosure can be a Walz XE-PAM pulse-amplitude-modulation fluorometer available from Heinz Waltz Gmbh, or a comparable device. Generally, the components of test unit 102 can be enclosed within a suitable container or case to protect the components from the surrounding environment.

In order to generate accurate fluorescence data, it is preferable to dark condition (i.e., reduce exposure of the water to light) the algae for a period of time before the algae enters fluorometer 230. In some embodiments, the dark conditioning can be accomplished by making coil 218, line 222, holding chamber 224, side arm 225 and line 226 opaque. In other embodiments, the components of test unit 102 can be enclosed in an opaque container or housing, which can provide sufficient dark conditioning. Additionally, the flow of water through coil 218 can be a function of the frequency in which tests are taken and the time interval between tests. Thus, since each test can take about 10 seconds or less, the theoretical flow rate of water to fluorometer 230 can be equal to approximately one sixth of a minute plus the time between tests, multiplied by the number of tests performed per minute. In some embodiments, this theoretical water flow rate can help determine the length of coil 218, which can assure the algae in the water has been "dark conditioned" for a sufficiently period of time. In some embodiments, the water can be dark conditioned from about 3 minutes to about 10 minutes, while in other embodiments the water can be dark conditioned from about 4 minutes to about 8 minutes prior to testing the water sample.

As shown in FIG. 2a, fluorometer exit line 242 can be provided to facilitate removal of water samples from fluorometer 230, and can provide a fluid flow pathway from fluorometer 230 to discharge line 220. Additionally, fluid flow out of fluorometer 230 through exit line 242 can be controlled by valve 240. In some embodiments, valve 240 can remain open and can be closed only during the analyzing process to halt the flow of water through fluorometer 230. Additionally, in some embodiments, valve 214, which normally directs flow of water from the pump to discharge line 220, can be positioned to direct water flow to coil 218 during testing cycles. In some embodiments, valve 214 can direct water to coil 218 only when necessary to supply water for testing, and thus the water located in fluorometer input line 226 can be under atmospheric pressure such that water flows to fluorometer 230 under the force of gravity.

Generally, it can be desirable to isolate and collect a water sample that has a fluorescence induction pattern that deviates a predetermined amount from a baseline induction pattern. In one embodiment, the collection of deviant samples can be achieved by actuation of solenoid 243 associated with valve 244, which is interposed in exit line 242. Actuation of solenoid 243 can redirect water flow from exit line 242 through a sample collection line to sample collection container 246. In some embodiments, sample collection container 246 can comprise a vial or the like. In some embodiments, a plurality of additional sample containers 247, each with an associated three way valve, such as valve 245, may be provided to permit the collection of multiple samples in the event a series of sample tests have deviated significantly from an established baseline. Each three way valve, such as valve 245, can be moved to permit communication exclusively with its associated container, while the three way valves associated with the other vials can be positioned to communicate with their respective line 242. In some embodiments, each sample container can be provided with a self sealing disconnect, such that each container can be safely removed and its contents analyzed to identify the potential toxic chemical present in the sample.

In general, sediment entrained in the water drawn from the water supply site can settle and collect in the bottom of holding chamber 224. As a result, it can be desirable to purge holding chamber 224 by periodically opening valve 252, which can transfer water and sediment located in holding chamber 224 into discharge line 250. While valve 252 is open for purging, valve 228 can be closed to reduce the possibility that sediment located in chamber 224 will be carried into fluorometer 230. Additionally, it may be desirable to clean fluorometer 230 with distilled water or other suitable liquids, in order to remove sediment or other contaminants that may have collected on the optical and/or light components. In some embodiments, this can be accomplished by providing distilled water container 260, which can be connected through conduit 262 to the top of the holding chamber 224. Additionally, valve 264 can be interposed in conduit 262 to regulate the flow of distilled water into the holding chamber 224, and ultimately into fluorometer 230. During cleaning, valve 262 can be opened to permit distilled water to flow into holding chamber 224, which can then flow through valve 228 into fluorometer 230. Additionally, the distilled water can flow out of fluorometer 230 via line 242 into the discharge line 220. After the flushing operation is completed, valve 228 can be closed and the valve 252 can be opened, which can facilitate moving any distilled water remaining in chamber 224 into discharge line 250. When the distilled water in chamber 224 has been drained, valve 252 can be closed and valve 228 can be opened so that testing operations can continue.

As shown in FIG. 2a, valve 266 can be provided in the discharge line 220 to regulate the flow of water through discharge line 220. Valve 266 can be closed to permit back flushing of the system. With valve 226 closed, the output from the pump can be forced to flow through line 242, which facilitates back flushing of line 242. The position of each of the aforementioned valves can be controlled by an associated solenoid, such as, for example, solenoid 216 that controls valve 214. Each of the solenoids can be connected to, and controlled by, a microprocessor-based controller in the electronic control module 238. The controller can be programmed to position the valves to permit desired water flow through test unit 102.

In some embodiments, the testing/analyzing of water samples in fluorometer 230 can comprise determining the optoelectronic fluorescence of algae, which are naturally present in the water supply. In general, algae will fluoresce when exposed to a sequence of pulsed light, followed by a saturation pulse of actinic light in the fluorometer. In some embodiments, the test sample can comprise a water sample from about 2 ml to about 10 ml, while in other embodiments the test sample can comprise a water sample of about 3 ml. Test conditions for monitoring the fluorescence of algae in water are generally described in U.S. Pat. No. 6,569,384 to Greenbaum et al., entitled "Tissue-Based Water Quality Biosensors For Detecting Chemical Warfare Agents," which is hereby incorporated by reference herein. The fluorescence induction pattern of each water sample can be measured by fluorometer 230, and the resulting data can be transmitted through data communication line 232 to a control module 238 and then through a data link having a 2-way external communication line 236 to a control system (FIG. 4), where the data can be compared against a database of established fluorescence baseline(s). Additionally or alternatively, data generated by test unit 102 can be compared against a database of established fluorescence baselines by a computer processor located within control module 238.

Figure 5:
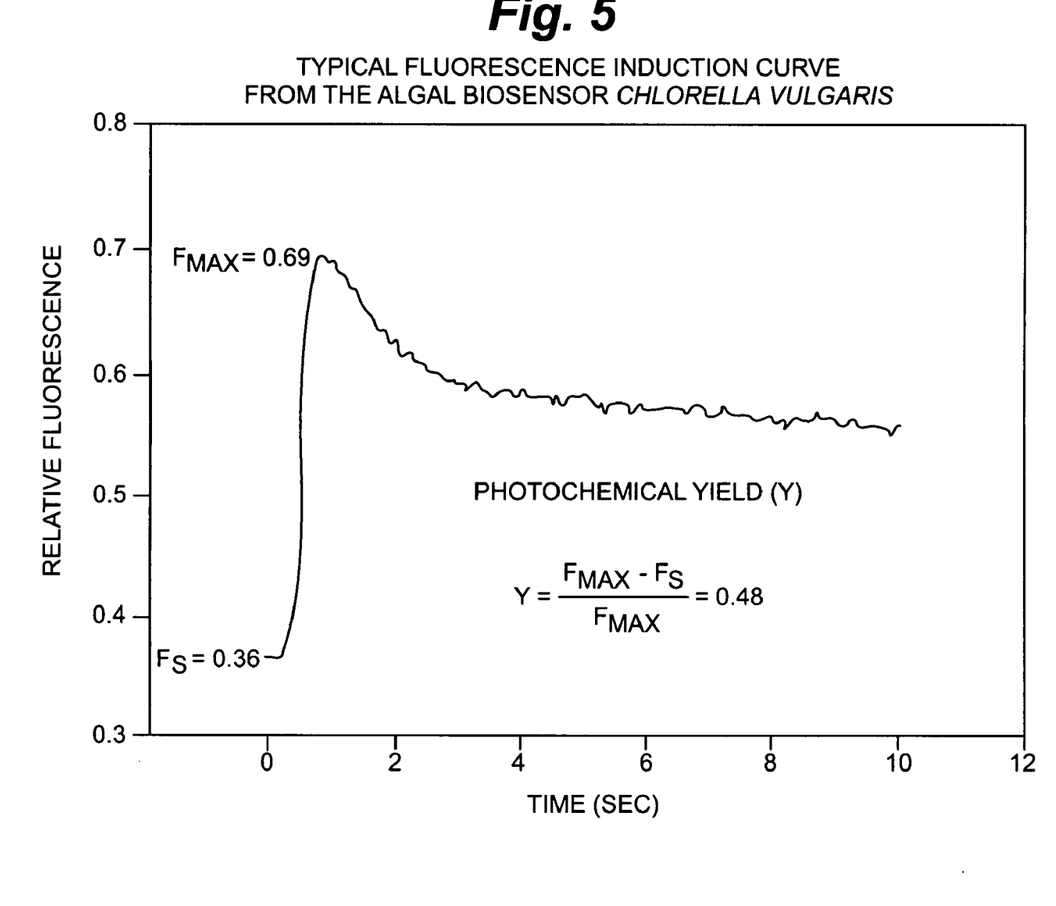
FIG. 5 shows a typical fluorescence induction curve for the algal biosensor *Chlorella vulgaris*.
Figure 6:
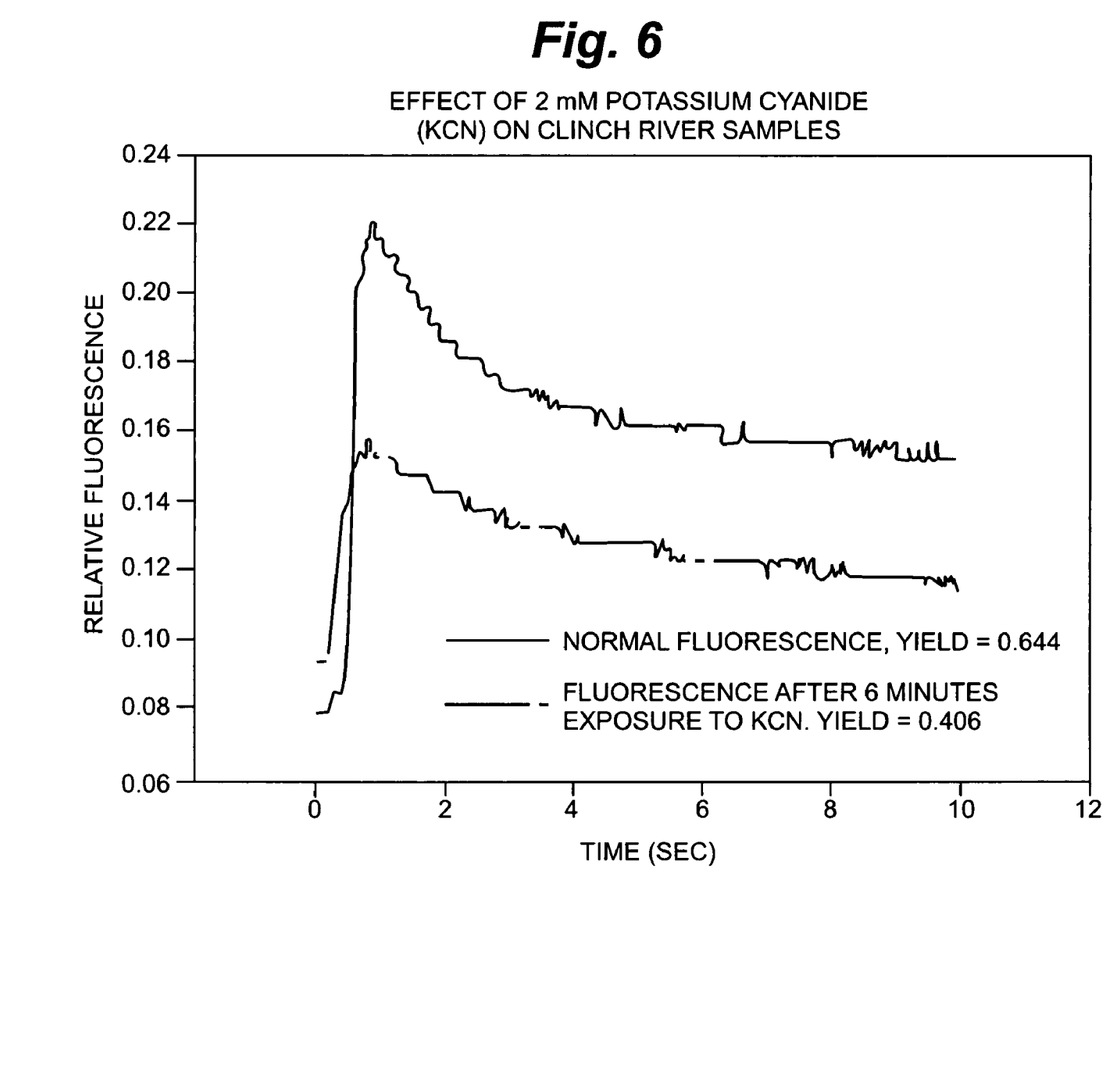
FIG. 6 shows the effect of 2 mM of Potassium Cyanide (KCN) on the fluorescence of a water sample taken from the Clinch River.

Predetermined deviations from the baseline can indicate that the algae are being stressed in some manner, which can be caused by the presence of toxic chemicals and/or biochemicals. If a deviant sample is detected, the deviant sample can be collected in sample container 246 to facilitate a detailed chemical analysis of the sample at a later time. Referring to FIGS. 5 and 6, FIG. 5 shows a typical fluorescence induction curve or pattern for Algal Biosensor Chlorella vulgaris, while FIG. 6 shows the effect of 2 mM Potassium cyanide (KCN) on a water sample taken from the Clinch river. As shown in FIG. 6, the presence of a small amount of Potassium cyanide can measurably lower the fluorescence of algae, which can facilitate real time detection of potentially toxic chemicals in a water supply.

Figure 2B:
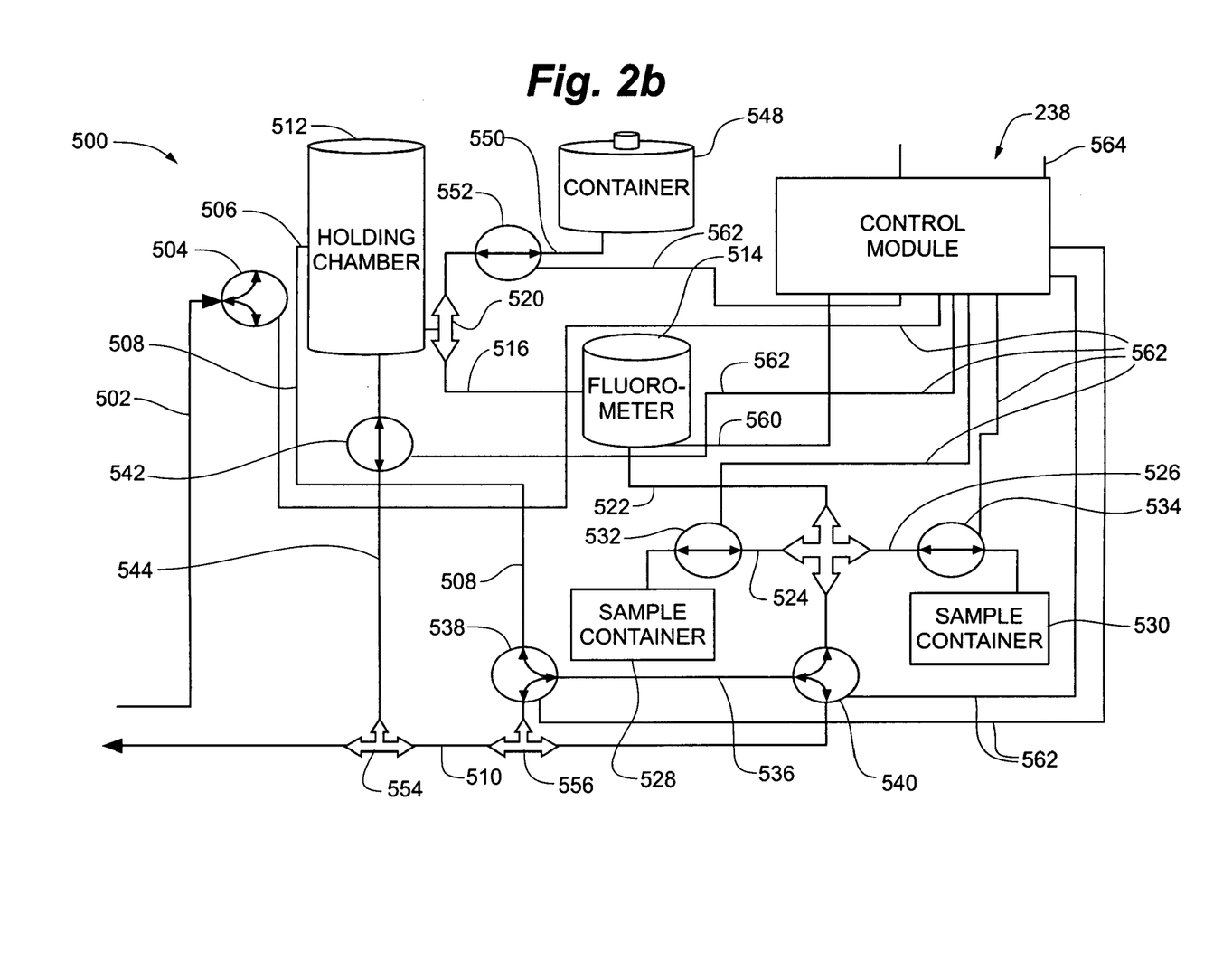
FIG. 2b is an alternate schematic diagram of a test unit that can be employed in the water monitoring systems of the present disclosure.

Referring to FIG. 2b, an alternate embodiment of a test unit 500 is shown comprising water intake line 502 connected to the output of a conventional pump (not shown). As described above, the intake of the conventional pump can be in free communication with, and can draw water from, a desired water supply site. As shown in FIG. 2b, valve 504 can regulate fluid flow between a first position, in which intake line 502 is connected to holding chamber input line 506, and a second position in which intake line 502 is connected to line 508, which can be connected to discharge line 510. Generally, holding chamber input line 506 can be connected to holding chamber 512. Holding chamber 512 can be connected to fluorometer 514 by holding chamber output line 516. Valve 520 can be provided to regulate fluid flow through output line 516 to fluorometer 514. Fluorometer 514 can also be connected to exit line 522, which can provide a fluid flow pathway to discharge line 510. In some embodiments, flow lines 524, 526 can provide fluid flow pathways from exit line 522 to sample collection containers 528, 530, respectively. Additionally, valves 532, 534 can be interposed in lines 524, 526 to regulate the flow of fluid through flow lines 524, 526, respectively.

As shown in FIG. 2b, flow line 536 can be provided to connect line 508 and exit line 522, which can provide a fluid flow pathway from line 508 to exit line 522. Additionally, valve 538 can be interposed at the intersection of flow line 508 and flow line 536, while valve 540 can be interposed at the intersection of line 508 and exit line 522. Thus, flow line 508 and valves 538, 540 permit back flushing of water into exit line 522 to clean out exit line 522. In some embodiments, holding chamber 512 can be provided with valve 542 and line 544, which can facilitate purging the contents of holding chamber 512 into discharge line 510. In some embodiments, container 548 can be provided to house distilled water or other suitable cleaning solutions. Container 548 can be connected to valve 520 by line 550. Additionally valve 552 can be interposed in line 550 to regulate the flow of fluid through line 550 to valve 520. Thus, distilled water or other suitable cleaning solutions can be introduced from container 548 into fluorometer 514 through lines 550 and line 516, which facilitates cleaning the optical and other components of fluorometer 514.

Valves 554, 556 can be interposed in discharge line 510 to regulate the flow of fluids through discharge line 510. Fluorometer 514 can be operably connected to control module 238 by line 560, which facilitates communicating water supply data to control module 238. As shown in FIG. 2b, control module 238 can be connected to the various valves by lines 562, which permits control module 238 to control the position of the valves of test unit 500 such that desired fluid flow through test unit 500 can be maintained. Generally, control module 238 can comprise a data link with a two external communication link 564, which facilitates communicating data generated by fluorometer 514 to control system 106.

Figure 3:
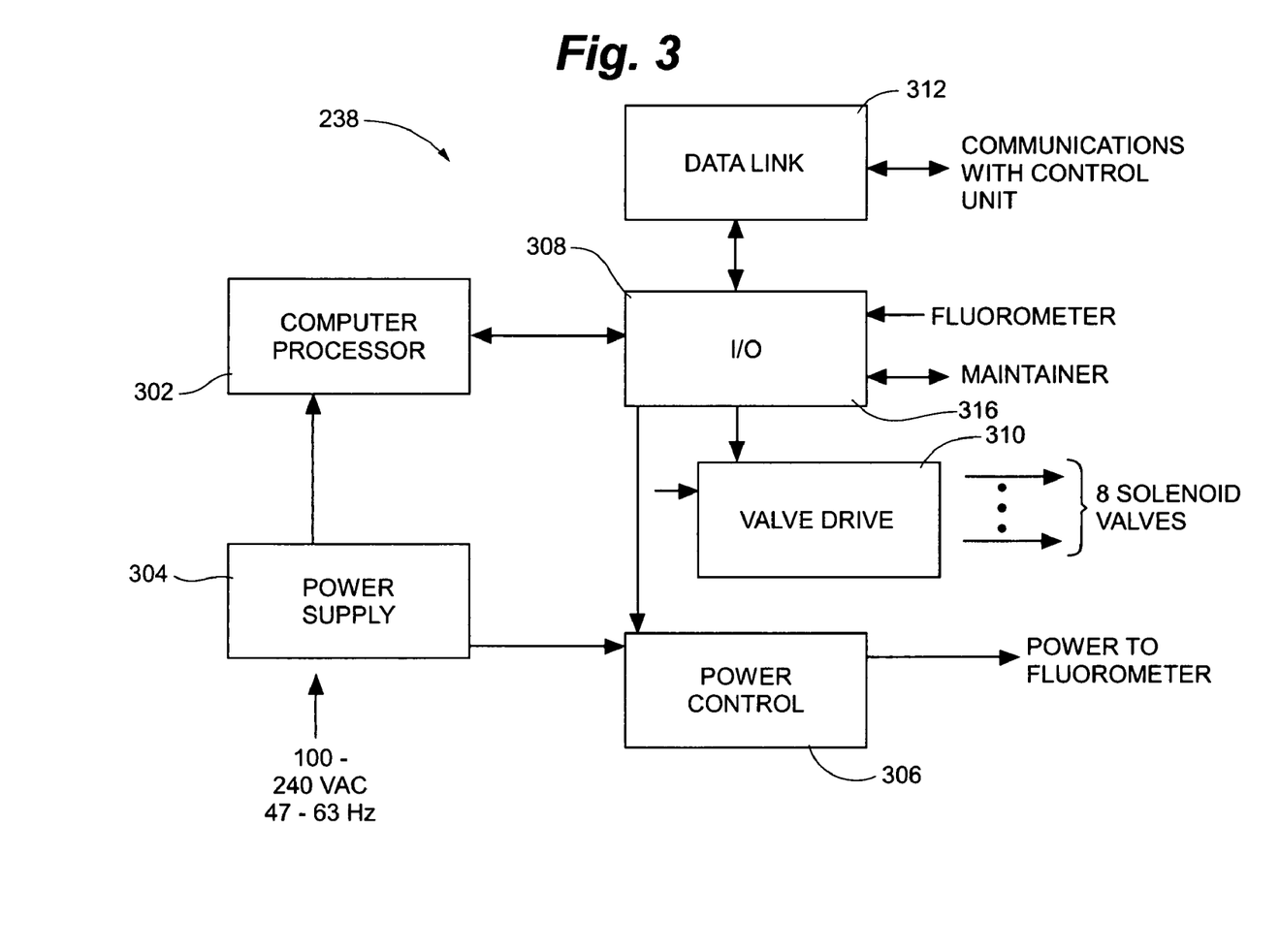
FIG. 3 is a block diagram of a control module that can be employed in the test units of the present disclosure.

As described above, test units 102, 500 can comprise an electronic control module 238, which can control the function of test units 102, 500. Moreover, control module 238 can be operably connected to the various solenoid and valve assemblies of test units 102, 500 by cables 250, 562, respectively, which allows control module 238 to control the flow of water through test units 102, 500. Referring to FIG. 3, a block diagram is shown for an embodiment of electronic control module 238. As shown in FIG. 3, electronic control module 238 can comprise a computer processor 302 operably connected to power supply 304, which can be operably connected to power control unit 306. Additionally, power control unit 306 can be connected to fluorometer 230 to provide power from power supply 304 to fluorometer 230. Computer processor 302 can be operably coupled to input/output device 308, which facilitates sending and receiving signals to and from computer processor 302. In general, any input/output device suitable for use in analytical monitoring equipment can be employed in control module 238. Suitable input/output devices include, for example, serial ports such as RS 485 and RS-232, parallel ports such as IEEE 488, USB ports, PCI bus and combinations thereof.

As shown in FIG. 3, input/output device 308 can be operably coupled with fluorometer 230, 514 such that water supply data can be sent from fluorometer 230, 514 to input/output device 308. Input/output device 308 can also be operably connected with valve driver 310, which can be connected to each of the solenoids associated with the valves of test unit 102, 500. Thus, computer processor 302 can send electrical signals through input/output device 308 to valve driver 310, such that computer processor 302 can control the function of the solenoids and the associated valves during operation of test units 102, 500. Input/output device 308 can also be in communication with data link 312, which can send data to the control system 106. Suitable data links include, for example, Ethernet connections, a fiber optic cables, wireless communication devices and combinations thereof. Thus, water supply data generated by fluorometer 230, 514 can be sent to input/output device 308, where the data can be routed to data link 312 such that the data can be transmitted to control system 106. Additionally, input/output device 308 can be in communication with power control unit 306 such that computer processor 302 can send signals to the power control unit 306 via input/output device 308. As shown in FIG. 3, a maintainer port 316 can be provided such that an external computer can be connected to input/output device 308. The external computer can be used to override the system controls during, for example, field testing procedures or the like.

Figure 4:
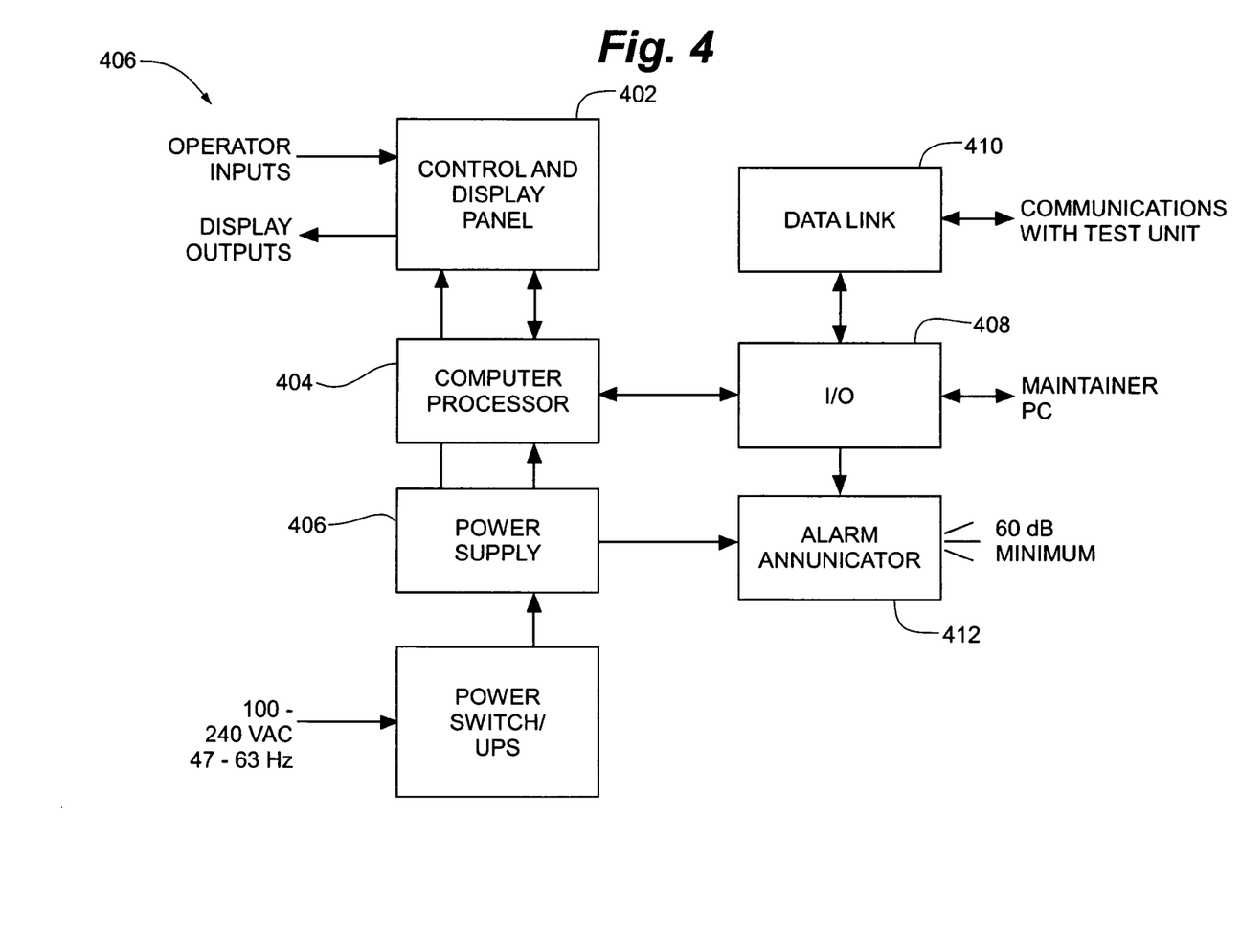
FIG. 4 is a block diagram of a remotely located control system that can be employed in the water monitoring systems of the present disclosure.

As described above, the water monitoring systems of the present disclosure can comprise a control system in communication with one or more test units, which facilitates continuously monitoring one or more water supply sources from a centralized location. In some embodiments, the control system can be a remotely located control system. Referring to FIG. 4 a block diagram of an embodiment of a control system 106 is shown comprising control and display panel 402 operably connected to computer processor 404. In some embodiments, control and display panel 402 can comprise a display device such as, for example, a computer monitor, and a user input device such as a keyboard, mouse, touchpad or combination thereof. Generally, computer processor 404 is operably connected to power supply 406 and input/output device 408. Suitable input/output devices for use in control system 106 are described above. Input/output device 408 can be in communication with data link 410, which can be in communication with data link 312 of one or more test units 102, 500. Data link 410 can comprise an Ethernet connection, a fiber optical cable, wireless communication device or a combination thereof. Thus, water supply data such as, for example, fluorescence induction data generated by one or more test units 102, 500 can be received by data link 410 and routed to computer processor 404 via input/output device 408. Input/output device 408 can also be connected to alarm enunciator 412, which facilitates connection of computer processor 404 and alarm enunciator 412.

Generally, computer processor 404 can process the water supply data transmitted from one or more test units 102, 500. In some embodiments, computer processor 404 can compare the fluorescence induction curve of a water sample to know baseline fluorescence patterns. If a particular fluorescence induction pattern from a water sample deviates from a baseline fluorescence pattern by a predetermined amount, computer processor 404 can send a signal to control and display panel 402 such that a visual warning is displayed on control and display panel 402. Additionally or alternatively, computer processor 404 can send a signal to alarm enunciator 412 such that an audio signal can alert the presence of a fluorescence induction pattern that is outside a predetermined deviation from a standard baseline fluorescence induction pattern.

In some embodiments, computer processor 404 can be in communication with a database of known toxin/water fluorescence induction curves, which facilitates analysis of potential toxins in a water supply. In these embodiments, if a fluorescence induction curve for a water sample is within a predetermined deviation from a known toxin/water fluorescence induction curve, computer processor 404 can send a signal to control and display panel 402 indicating that that a potential toxin has been detected, and processor 404 can also indicate that the fluorescence curve is a potential match for a particular toxin.

During operation, water from a desired water supply site 104 can be introduced, by a pump, into a test unit, such as the test units described above in FIGS. 2*a* and 2*b*, through the water intake line, and can be directed to a holding chamber. Alternatively, water introduced into the test unit can be directed to a discharge line. In some modes of operation, water can be continuously pumped from the water source into the intake line, while in other embodiments water can be intermittently pumped into the intake line. As described above, during testing cycles water located in holding chamber can be introduced into the fluorometer, which facilitates testing of the water sample. Once testing of particular water sample has been completed by the fluorometer, the water sample located in the fluorometer can be directed through an exit line to a discharge line. Fluorescence induction data generated by the fluorometer can be sent to a control module, where the data can be transmitted by a data link to a data link of a control system. Fluorescence induction data transmitted to the control system can be compared against baseline fluorescence induction patterns a by processor operably connected to the data link to determine if a deviant sample is present. In the event a deviant sample is detected, a signal can be sent from the processor to a control and display panel and/or an alarm enunciator such that a visual and/or audio signal can alert the detection of a deviant water sample. Additionally, in the event a deviant sample is detected by the control system, the water sample causing the alert can be directed into a sample collection container, which facilitates collection of the deviant water sample for further chemical analysis.

The embodiments above are intended to be illustrative and not limiting. Additional embodiments are within the claims. Although the present invention has been described with reference to particular embodiments, workers skilled in the art will recognize that changes may be made in form and detail without departing from the spirit and the scope of the invention.

The invention claimed is:

1. A water supply monitoring system comprising:
   a test unit comprising a housing, a plumbing system that can intake water from a water source into the housing, wherein the plumbing system comprises a pump, an intake line connected to the pump, said intake line including an intake valve that regulates fluid flow through the intake line to a first discharge line, and a holding chamber, said holding chamber fluidly connected to a holding chamber input line to the intake line, the holding chamber further including an opening fluidly connected to a second discharge line so as to selectively purge the contents of the holding chamber, a fluorometer located within the housing connected to the plumbing system, and a control module comprising a first computer processor and a first data link operably connected to the first computer processor, wherein the plumbing system provides a fluid flow pathway to the fluorometer, and wherein the fluorometer is operably connected to the first data link such that fluorescence induction data generated by the fluorometer can be communicated to the first data link; and
   a remotely located control system comprising a second data link in communication with the first data link, a second computer processor operably connected to the second data link, and a control and display panel operably connected to the second computer processor, wherein the first data link can communicate the fluorescence induction data to the second data link, and wherein the fluorescence induction data can be communicated from the second data link to the second computer processor.

2. The water supply monitoring system of claim 1 wherein the plumbing system further comprises a holding chamber output line that provides a fluid flow pathway from the holding chamber to the fluorometer, and wherein an input valve is interposed in the holding container output line to regulate the flow of water from the holding chamber to the fluorometer.

3. The water supply monitoring system of claim 2 wherein the fluorometer is fluidly connected to an exit line that is connected to the first discharge line.

4. The water supply monitoring system of 3 wherein a first output valve is interposed in the exit line to regulate fluid flow through the exit line.

5. The water supply monitoring system of claim 4 further comprising a sample collection line connected to the exit line, a sample collection container in communication with the sample collection line and a second output valve interposed in the exit line, wherein the sample collection line provides a fluid flow pathway from the exit line to the sample collection container, and wherein the second output valve regulates fluid flow from the exit line to the sample collection container.

6. The water supply monitoring system of claim 5 wherein the control module further comprises a valve drive operably connected to the intake valve, the input valve, the first output valve and the second output valve, wherein the valve drive is operably connected to the first computer processor such that the first computer processor can communicate with the valve drive and control the function of the intake valve, the input valve, the first output valve and the second output valve.

7. The water supply monitoring system of claim 1 wherein the holding chamber input line and the holding chamber are opaque.

8. The water supply monitoring system of claim 1 wherein the fluorometer comprises a pulse-amplitude-modulation fluorometer.

9. The water supply monitoring system of claim 1 wherein the remotely located control system further comprises an alarm enunciator operably connected to the second computer processor, wherein the second computer processor can send a signal to the alarm enunciator to sound an audio alert if a deviant water sample is detected.

10. A method of monitoring a water supply comprising:
a test unit comprising a housing, a plumbing system that can intake water from a water source into the housing, a fluorometer located within the housing connected to the plumbing system, and a control module comprising a first computer processor and a first data link operably connected to the first computer processor, wherein the plumbing system provides a fluid flow pathway to the fluorometer, and wherein the fluorometer is operably connected to the first data link such that fluorescence induction data generated by the fluorometer can be communicated to the first data link, wherein the plumbing system comprises a pump, an intake line connected to the pump, said intake line including an intake valve that regulates fluid flow through the intake line to a first discharge line, and a holding chamber, said holding chamber fluidly connected to a holding chamber input line to the intake line, the holding chamber further including an opening fluidly connected to a second discharge line so as to selectively purge the contents of the holding chamber; and
communicating fluorescence induction data of a water sample generated by a test unit to a remotely located control system, wherein the control system comprises a control and display panel, a computer processor and a data link, wherein the computer processor is operably connected to the data link such that signals received by the data link can be communicated to the computer processor, and wherein the control and display panel is operably connected to the computer processor to receive signals from the computer processor.

11. The method of claim 10 further comprising processing the fluorescence induction data at the computer processor.

12. The method of claim 10 wherein the processing comprises comparing the transmitted fluorescence induction data against baseline fluorescence induction data to determine if a deviant sample is present.

13. The method of claim 12 further comprising sending a signal from the computer processor to the control and display panel if a deviant sample is detected, wherein the control and display panel displays a visual warning to alert the presence of a deviant sample.

14. The method of claim 12 wherein the control system further comprises an alarm enunciator operably connected to the computer processor, wherein the alarm enunciator can sound an audio alert if a deviant water sample is detected.

15. The method of claim 14 further comprising sending a signal from the computer processor to the alarm enunciator if a deviant sample is detected.

16. The method of claim 10 wherein the test unit comprises a sample collection container, which facilitates collection of a deviant water sample, wherein the method further comprises collecting the deviant sample in the sample collection container.

* * * * *